(12) United States Patent
Reddy et al.

(10) Patent No.: US 7,053,123 B2
(45) Date of Patent: May 30, 2006

(54) SUBSTITUTED (E)-STYRYL BENZYLSULFONES FOR TREATING PROLIFERATIVE DISORDERS

(75) Inventors: E. Premkumar Reddy, Villanova, PA (US); M. V. Ramana Reddy, Upper Darby, PA (US)

(73) Assignee: Temple University-of the Commonwealth System of Higher Education, Philadelphia, PA (US)

( * ) Notice: Subject to any disclaimer, the term of this patent is extended or adjusted under 35 U.S.C. 154(b) by 38 days.

(21) Appl. No.: 10/398,545

(22) PCT Filed: Oct. 5, 2001

(86) PCT No.: PCT/US01/31337

§ 371 (c)(1),
(2), (4) Date: Aug. 28, 2003

(87) PCT Pub. No.: WO02/28828

PCT Pub. Date: Apr. 11, 2002

(65) Prior Publication Data

US 2005/0101528 A1 May 12, 2005

Related U.S. Application Data

(60) Provisional application No. 60/238,222, filed on Oct. 5, 2000.

(51) Int. Cl.
A61K 31/10 (2006.01)
C07C 317/10 (2006.01)

(52) U.S. Cl. ............... 514/710; 514/646; 568/30; 568/33; 568/34; 568/35; 564/441; 564/442

(58) Field of Classification Search ............ 568/30, 568/33, 34, 35; 564/440, 441, 442; 514/646, 514/710
See application file for complete search history.

(56) References Cited

U.S. PATENT DOCUMENTS

| | | | |
|---|---|---|---|
| 2,532,612 A | 12/1950 | Doumani | 568/60 |
| 3,185,743 A | 5/1965 | Combe et al. | 585/638 |
| 3,418,101 A | 12/1968 | Buchholtz et al. | 504/162 |
| 3,463,774 A | 8/1969 | Wilhelm et al. | 540/490 |
| 3,514,386 A | 5/1970 | Oswald et al. | 204/157.73 |
| 3,917,714 A | 11/1975 | Richmond | 568/33 |
| 4,161,407 A | 7/1979 | Campbell | 430/621 |
| 4,386,221 A | 5/1983 | Hyatt et al. | 568/28 |
| 4,937,388 A | 6/1990 | Bushell et al. | 560/56 |
| 5,659,087 A | 8/1997 | Aikins et al. | 568/27 |
| 5,733,909 A | 3/1998 | Black et al. | 514/238.8 |
| 6,030,961 A * | 2/2000 | Nudelman et al. | 514/120 |
| 6,201,154 B1 | 3/2001 | Reddy et al. | 568/28 |
| 6,359,013 B1 | 3/2002 | Reddy et al. | 514/710 |
| 6,414,034 B1 | 7/2002 | Reddy et al. | 514/710 |
| 6,486,210 B1 | 11/2002 | Reddy et al. | 514/708 |
| 6,541,475 B1 * | 4/2003 | Reddy et al. | 514/252.12 |
| 6,548,553 B1 | 4/2003 | Reddy et al. | 514/710 |
| 6,576,675 B1 | 6/2003 | Reddy et al. | 514/710 |
| 6,656,973 B1 * | 12/2003 | Cosenza et al. | 514/710 |
| 6,667,346 B1 | 12/2003 | Reddy et al. | 514/710 |
| 6,762,207 B1 * | 7/2004 | Reddy et al. | 514/709 |

FOREIGN PATENT DOCUMENTS

| | | |
|---|---|---|
| WO | WO 99/18068 | 4/1999 |
| WO | WO 01/26645 | 4/2001 |

OTHER PUBLICATIONS

Richard B. Silverman, The Organic Chemistry of Drug Design and Drug Action, 1992, pp. 15-22.*
U.S. Appl. No. 09/937,684, filed Sep. 28, 2001, Reddy et al.
Reddy et al., *Org. Prep. Proc. Int.*, 20(3):205-212 (1988).
Reddy et al., *Sulfur Lett.*, 13(2):83-90 (1991).
Reddy and Reddy, *Acta Chim. Acad. Sci. Hung.*, 115(3):269-271 (1984).
Reddy et al., *Phosphorus, Sulfur Silicon Relat. Elem.*, 60:209-214 (1991).
Reddy and Reddy, *Acta Chim. Acad. Sci. Hung.*, 120(4):275-280 (1985).
Reddy and Reddy, *Synthesis* No. 4, 322-323 (1984).
Reddy et al., *Sulfur Lett.*, 7(2):43-48 (1987).
Reddy et al., *Phosphorus, Sulfur, and Silicon*, 53(1-4):285-290 (1990).

(Continued)

Primary Examiner—Rosalynd Keys
(74) Attorney, Agent, or Firm—Drinker Biddle & Reath LLP; Daniel A. Monaco, Esq.

(57) ABSTRACT

(E)-Styryl benzylsulfones useful as antiproliferative agents, including, for example, anticancer agents, are provided according to formula I: wherein: $R_1$ is selected from the group consisting of halogen, C1–C6 alkoxy, nitro, phosphonato, amino, sulfamyl, carboxy, acetoxy and dimethylamino (C2–C6 alkoxy); and $R_2$ and $R_3$ are independently selected from the group consisting of halogen, C1–C6 alkoxy, C1–C6 alkyl, nitro, cyano, hydroxyl, phosphonato, amino, sulfamyl, carboxy, acetoxy, and dimethylamino (C2–C6 alkoxy); provided: $R_1$ may not be halogen when $R_2$ and $R_3$ are both halogen; $R_2$ may not be 2-halogen when $R_3$ is 4-halogen; or a pharmaceutically acceptable salt thereof; or formula II: wherein: $R_4$ is selected from the group consisting of C1–C6 alkoxy, phosphonato, amino, sulfamyl, carboxy, acetoxy and dimethylamino (C2–C6 alkoxy); $R_6$ is selected from the group consisting of nitro, hydrogen, phosphonato, amino, sulfamyl, carboxy, acetoxy and dimethylamino (C2–C6 alkoxy); and $R_7$ is selected from the group consisting of halogen, C1–C6 alkoxy, C1–C6 alkyl, nitro, cyano, hydroxy, phosphonato, amino, sulfamyl, carboxy, acetoxy, dimethylamino (C2–C6 alkoxy) and trifluoromethyl; provided $R_5$ and $R_6$ may not be hydrogen in the same compound; or a pharmaceutically acceptable salt thereof.

18 Claims, 1 Drawing Sheet

OTHER PUBLICATIONS

Makosza and Krylova, *Liebigs Ann./Recueil*, 2337-2340 (1997).
Reddy et al., *Acta Chim. Hung.*, 131(1):83-92 (1994).
Benati, et al., *J. Org. Chem.*, 59:2818-2823 (1994).
Tanaka et al., Agric. Biol. Chem. 41, 1953-1959, 1977.
Baliah and Rathinasamy, *Indian J. Chem.* (1971), 9:220-225.
Kamigata et al., *Phosphorous and Sulfer*, (1984), 20:139-144.
CA:120:323356 abs of Reddy et al., *Sulf. Lett.* (1993), 16(5-6), 227-35.
CA:100:67921 abs of Takiwa et al., *Chem. Lett.* (1983), 9:1351-4.
CA:124:175763, abs of Reddy et al., *Indian J. Heterocyclo. Chem.*, (1995), 5(1), 11-14.
CA:124:146025, abs of Reddy et al., *Indian J. Heterocycl. Chem.* (1995), 4(4), 259-264.
CA:126:166162, abs of Thompson et al., *Cancer Res.*, (1997) 57(2), 267-271.
CA:122:132682 abs of Reddy et al., *Phosphorus, Sulfur Silicon Relat. Elem.* (1994), 90(1-4), 1-10.
CA:124:8731 abs of Reddy et al., *Indian J. Chem. Sect. B: Org. Chem. Incl. Med. Chem.* (1995) 34B(9), 816-22.
CA:76:121420 abs of Findlay et al. *Brit J. Dermatol.*, Suppl. (1971), No. 7, 44-9.
CA:105:133446 abs of Naidu et al., *Proc. Indian Acad. Sci., Chem. Sci* (1985), 95(4), 391-5.
CA:126:185889 abs of Japanese Pat. App. 09-03,037 (Jan. 7, 1997).
CA:132:263142 abs of Hillaire et al., *Pathol. Biol.*(1999), 47(9),895-902.
CA:130:336836 abs of Olson, *Med. Hypotheses* (1999), 51(6), 493-498.
CA:127:33922 abs of Evans and Taylor, *Tetrahedron Lett.* (1997), 3055-3058.
CA:125:327911 abs of Riad et al., *Egypt J. Chem.*(1996), 39(4), 353-364.
CA:120:210378 abs of Cheng and Hwang,*J. Chin. Biochem. Soc.* (1993),22(1), 27-35.
CA:103:141088 abs of Janczewski and Ksiezopolski, *Pol. J. Chem.* (1984),58(1-2-3), 103-16.
CA:121:256180 abs of Li et al., *Bioorg. Med. Chem. Lett.* (1994),4(13), 1585-90.
Reddy M V et al, "Synthesis of some novel .alpha.,.beta.-ethylenic sulfones", *Phosphorus, Sulfur Silicon Relat, Elem.* 60(3-4):209-214 (1991).
Reddy D et al, "Synthesis and spectral studies of some unsaturated sulfones", *Phosphorus Sulfur*, 16(3):293-8 (1983).
Reddy D et al, "Cyclopropanation of some .alpha.,.beta.-unsaturated sulfones", *Indian J. Chem*, 19B(7):563-6 (1980).

* cited by examiner

SUBSTITUTED (E)-STYRYL BENZYLSULFONES FOR TREATING PROLIFERATIVE DISORDERS

The benefit of the filing date of U.S. Provisional Application Ser. No. 60/238,222, filed Oct. 5, 2000, is hereby claimed. The entire disclosure of the aforesaid application is incorporated herein by reference.

FIELD OF THE INVENTION

The invention relates to compositions and methods for the treatment of cancer and other proliferative disorders.

BACKGROUND OF THE INVENTION

Extracellular signals received at transmembrane receptors are relayed into the cells by the signal transduction pathways (Pelech et al., Science 257:1335 (1992)) which have been implicated in a wide array of physiological processes such as induction of cell proliferation, differentiation or apoptosis (Davis et al., J. Biol. Chem. 268:14553 (1993)). The Mitogen Activated Protein Kinase (MAPK) cascade is a major signaling system by which cells transduce extracellular cues into intracellular responses (Nishida et al., Trends Biochem. Sci. 18:128 (1993); Blumer et al., Trends Biochem. Sci. 19:236 (1994)). Many steps of this cascade are conserved, and homologous for MAP kinases have been discovered in different species.

In mammalian cells, the Extracellular-Signal-Regulated Kinases (ERKs), ERK-1 and ERK-2 are the archetypal and best-studied members of the MAPK family, which all have the unique feature of being activated by phosphorylation on threonine and tyrosine residues by an upstream dual specificity kinase (Posada et al., Science 255:212 (1992); Biggs III et al., Proc. Natl. Acad. Sci. USA 89:6295 (1992); Garner et al., Genes Dev. 6:1280 (1992)).

Recent studies have identified an additional subgroup of MAPKs, known as c-Jun NH2-terminal kinases 1 and 2 (JNK-1 and JNK-2), that have different substrate specificities and are regulated by different stimuli (Hibi et al., Genes Dev. 7:2135 (1993)). JNKs are members of the class of stress-activated protein kinases (SPKs). JNKs have been shown to be activated by treatment of cells with UV radiation, pro-inflammatory cytokines and environmental stress (Derijard et al., Cell 1025 (1994)). The activated JNK binds to the amino terminus of the c-Jun protein and increases the protein's transcriptional activity by phosphorylating it at ser63 and ser73 (Adler et al., Proc. Natl. Acad. Sci. USA 89:5341 (1992); Kwok et al., Nature 370:223 (1994)).

Analysis of the deduced primary sequence of the JNKs indicates that they are distantly related to ERKs (Davis, Trends Biochem. Sci. 19:470 (1994)). Both ERKs and JNKs are phosphorylated on Tyr and Thr in response to external stimuli resulting in their activation (Davis, Trends Biochem. Sci. 19:470 (1994)). The phosphorylation (Thr and Tyr) sites, which play a critical role in their activation are conserved between ERKs and JNKs (Davis, Trends Biochem. Sci. 19:470 (1994)). However, these sites of phosphorylation are located within distinct dual phosphorylation motifs: Thr-Pro-Tyr (JNK) and Thr-Glu-Tyr (ERK). Phosphorylation of MAPKs and JNKs by an external signal often involves the activation of protein tyrosine kinases (PTKs) (Gille et al., Nature 358:414 (1992)), which constitute a large family of proteins encompassing several growth factor receptors and other signal transducing molecules.

Protein tyrosine kinases are enzymes which catalyze a well defined chemical reaction: the phosphorylation of a tyrosine residue (Hunter et al., Annu Rev Biochem 54:897 (1985)). Receptor tyrosine kinases in particular are attractive targets for drug design since blockers for the substrate domain of these kinases is likely to yield an effective and selective antiproliferative agent. The potential use of protein tyrosine kinase blockers as antiproliferative agents was recognized as early as 1981, when quercetin was suggested as a PTK blocker (Graziani et al., Eur. J. Biochem. 135: 583–589 (1983)).

The best understood MAPK pathway involves extracellular signal-regulated kinases which constitute the Ras/Raf/MEK/ERK kinase cascade (Boudewijn et al., Trends Biochem. Sci. 20, 18 (1995)). Once this pathway is activated by different stimuli, MAPK phosphorylates a variety of proteins including several transcription factors which translocate into the nucleus and activate gene transcription. Negative regulation of this pathway could arrest the cascade of these events.

What are needed are new anticancer chemotherapeutic agents which target receptor tyrosine kinases and which arrest the Ras/Raf/MEK/ERK kinase cascade. Oncoproteins in general, and signal transducing proteins in particular, are likely to be more selective targets for chemotherapy because they represent a subclass of proteins whose activities are essential for cell proliferation, and because their activities are greatly amplified in proliferative diseases.

What is also needed are new cell antiproliferative agents, and anticancer therapeutics in particular, which are highly selective in the killing of proliferating cells such as tumor cells, but not normal cells.

SUMMARY OF THE INVENTION

It is an object of the invention to provide compounds, compositions and methods for the treatment of cancer and other proliferative diseases. The biologically active compounds are in the form of styryl benzylsulfones.

It is an object of the invention to provide compounds which are selective in killing tumor cells but not normal cells.

According to one embodiment, compounds of the invention have the formula I:

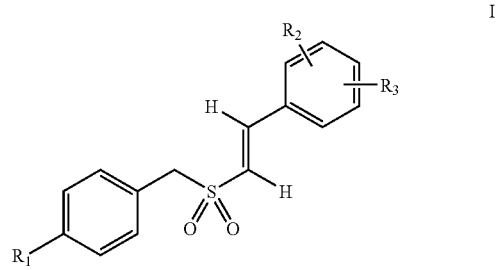

wherein:

$R_1$ is selected from the group consisting of halogen, C1–C6 alkoxy, nitro, phosphonato, amino, sulfamyl, carboxy, acetoxy, and dimethylamino(C2–C6 alkoxy); and $R_2$ and $R_3$ are independently selected from the group consisting of halogen, C1–C6 alkoxy, C1–C6 alkyl, nitro, cyano, hydroxy, phosphonato, amino, sulfamyl, carboxy, acetoxy, and dimethylamino(C2–C6 alkoxy);

provided:

$R_1$ may not be halogen when $R_2$ and $R_3$ are both halogen;

$R_2$ may not be 2-halogen when $R_3$ is 4-halogen;

or a pharmaceutically acceptable salt thereof.

According to one embodiment of formula I compounds, $R_1$ is selected from the group consisting of halogen, C1–C6 alkoxy, nitro, phosphonato, amino, sulfamyl, acetoxy, and dimethylamino(C2–C6 alkoxy); and $R_2$ and $R_3$ are independently selected from the group consisting of halogen, C1–C6 alkoxy, C1–C6 alkyl, nitro, cyano, hydroxy, phosphonato, amino, sulfamyl, acetoxy, and dimethylamino(C2–C6 alkoxy).

According to one preferred embodiment of formula I compounds, $R_1$ is selected from the group consisting of halogen and C1–C6 alkoxy, and $R_2$ and $R_3$ are independently selected from the group consisting of hydroxy, nitro and C1–C6 alkoxy. According to a further preferred embodiment, $R_1$ is C1–C6 alkoxy, and $R_2$ and $R_3$ are C1–C6 alkoxy. Most preferably, $R_2$ and $R_3$ together represent 3,4-dialkoxy or 2,6-dialkoxy substitution.

The various alkoxy groups may be the same or different.

According to another embodiment, compounds of the invention have the formula II:

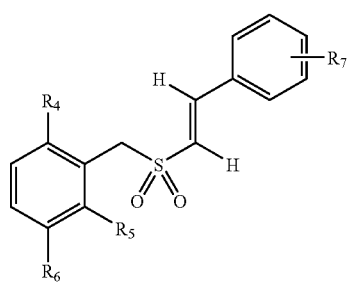

wherein:

$R_4$ is selected from the group consisting of C1–C6 alkoxy, nitro, phosphonato, amino, sulfamyl, carboxy, acetoxy, and dimethylamino(C2–C6 alkoxy);

$R_5$ is selected from hydrogen, C1–C6 alkoxy, phosphonato, amino, sulfamyl, carboxy, acetoxy, and dimethylamino (C2–C6 alkoxy); and $R_6$ is selected from nitro, hydrogen, phosphonato, amino, sulfamyl, carboxy, acetoxy, and dimethylamino(C2–C6 alkoxy); and $R_7$ is selected from the group consisting of halogen, C1–C6 alkoxy, C1–C6 alkyl, nitro, cyano, hydroxy, phosphonato, amino, sulfamyl, carboxy, acetoxy, dimethylamino (C2–C6 alkoxy) and trifluoromethyl;

provided $R_5$ and $R_6$ may not be hydrogen in the same compound.

According to one embodiment of formula II compounds, $R_4$ is selected from the group consisting of C1–C6 alkoxy, nitro, phosphonato, amino, sulfamyl, acetoxy, and dimethylamino(C2–C6 alkoxy); $R_5$ is selected from hydrogen, C1–C6 alkoxy, phosphonato, amino, sulfamyl, carboxy, acetoxy, and dimethylamino(C2–C6 alkoxy); $R_6$ is selected from nitro, hydrogen, phosphonato, amino, sulfamyl, acetoxy, and dimethylamino(C2–C6 alkoxy); and $R_7$ is selected from the group consisting of halogen, C1–C6 alkoxy, C1–C6 alkyl, nitro, cyano, hydroxy, phosphonato, amino, sulfamyl, acetoxy, dimethylamino(C2–C6 alkoxy) and trifluoromethyl.

According to one preferred embodiment of formula II compounds, $R_5$ is hydrogen and $R_6$ is nitro, or $R_5$ is C1–C6 alkoxy and $R_6$ is hydrogen; and $R_7$ is selected from the group consisting of halogen, nitro and C1–C6 alkoxy.

According to another embodiment of the invention, the compounds (E)-2-nitrostyryl-2,4-dichlorobenzylsulfone, (E)-3-nitrostyryl-2,4-dichlorobenzylsulfone and (E)-2,6-dimethoxystyryl-2-methoxybenzylsulfone are provided, and pharmaceutically acceptable salts thereof.

The styryl benzylsulfones are characterized by cis-trans isomerism resulting from the presence of a double bond. The compounds are named according to the Cahn-Ingold-Prelog system, the IUPAC 1974 Recommendations, Section E: Stereochemistry, in *Nomenclature of Organic Chemistry*, John Wiley & Sons, Inc., New York, N.Y., 4$^{th}$ ed., 1992, p. 127–138. Steric relations around a double bond are designated as "Z" or "E". The compounds of the present invention have the E configuration.

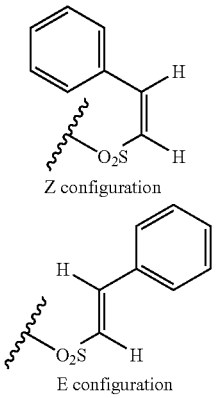

The term "alkyl", by itself or as part of another substituent means, unless otherwise stated, a straight or branched chain hydrocarbon radical, including di- and multi-radicals, having the number of carbon atoms designated (i.e. C1–C6 means one to six carbons) and includes straight or branched chain groups. Most preferred is C1–C3 alkyl, particularly ethyl and methyl.

The term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy and the higher homologs and isomers. Preferred are C1–C3 alkoxy, particularly ethoxy and methoxy.

By "halogen" is meant fluorine, chlorine, bromine or iodine.

By "dimethylamino(C2–C6 alkoxy)" is meant $(CH_3)_2N(CH_2)_nO$— wherein n is from 2 to 6. Preferably, n is 2 or 3. Most preferably, n is 2, that is, the group is the dimethylaminoethoxy group, that is, $(CH_3)_2NCH_2CH_2O$—.

By "phosphonato" is meant the group —$PO(OH)_2$.

By "sulfamyl" is meant the group —$SO_2NH_2$.

Where a substituent on the benzyl or styryl nucleus is an alkoxy group, the carbon chain may be branched or straight, with straight being preferred. Preferably, the alkoxy groups comprise C1–C3 alkoxy, most preferably methoxy.

A pharmaceutical composition is also provided comprising a pharmaceutically acceptable carrier and one or more compounds of formula I or II above, or a pharmaceutically acceptable salt of such compound.

According to another embodiment of the invention, a method of treating an individual for a proliferative disorder, particularly cancer, is provided, comprising administering to said individual an effective amount of a compound according to formula I or II, or a pharmaceutically acceptable salt of such compound, alone or in combination with a pharmaceutically acceptable carrier.

In another embodiment of the invention, a method of inhibiting growth of tumor cells in an individual afflicted with cancer is provided comprising administering to said individual an effective amount of a compound according to formula I or II, or a pharmaceutically acceptable salt of such compound, alone or in combination with a pharmaceutically acceptable carrier.

In another embodiment, a method of inducing apoptosis of cancer cells, more preferably tumor cells, in an individual afflicted with cancer is provided, comprising administering to said individual an effective amount of a compound according to formula I or II, or a pharmaceutically acceptable salt of such compound, alone or in combination with a pharmaceutically acceptable carrier.

The compounds (E)-2-nitrostyryl-2,4-dichlorobenzylsulfone, (E)-3-nitrostyryl-2,4-dichlorobenzylsulfone and (E)-2,6-dimethoxystyryl-2-methoxybenzylsulfone, and pharmaceutically acceptable salts thereof, may also be used to form pharmaceutical compositions, and may be utilized in the practice of the aforesaid methods for treating proliferative disorders, for inhibiting growth of tumor cells, and for inducing apoptosis of cancer cells.

DETAILED DESCRIPTION OF THE INVENTION

Figure 1:
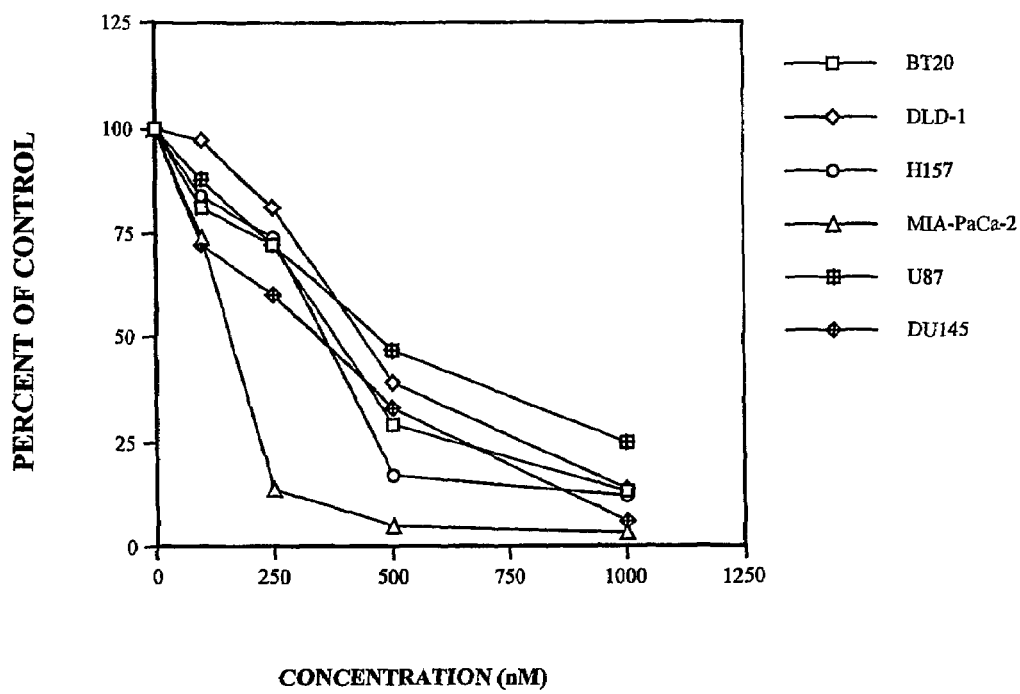
FIG. 1 shows the effect of (E)-2,6-dimethoxystyryl-4-methoxybenzylsulfone on the growth of cells of the indicated tumor cell lines. Values are plotted as the percent of drug-treated cells remaining viable compared to DMSO-treated cells of the same type.

According to the present invention, certain substituted styryl benzylsulfone derivatives selectively kill various tumor cell types without killing normal cells.

Without wishing to be bound by any theory, it is believed that the compounds affect the MAPK signal transduction pathway, thereby affecting tumor cell growth and viability. This cell growth inhibition is associated with regulation of the ERK and JNK types of MAPK. Without wishing to be bound by any theory, the styryl sulfones of the present invention may block the phosphorylating capacity of ERK-2.

The compounds of the invention inhibit the proliferation of tumor cells by inducing cell death.

The compounds of the invention are believed effective against broad spectrum of cancer types of diverse histologic subtype and origin. Cancer types which may be treated by the present compounds include those cancers listed and described in the National Cancer Institute's "CancerNet" at http://cancernet.nci.nih.gov/pdq/pdq_treatment.shtml, which is herein incorporated by reference in its entirety.

For example, the compounds of the invention may be used to kill primary or metastatic tumor or neoplastic cells in cancers of at least the following histologic subtypes: sarcoma (cancers of the connective and other tissue of mesodermal origin); melanoma (cancers deriving from pigmented melanocytes); carcinoma (cancers of epithelial origin); adenocarcinoma (cancers of glandular epithelial origin); cancers of neural origin (glioma/glioblastoma and astrocytoma); and hematological neoplasias, such as leukemias and lymphomas (e.g., acute lymphoblastic leukemia, chronic lymphocytic leukemia, and chronic myelocytic leukemia).

The present compounds may also be used to kill primary or metastatic tumor or neoplastic cells in cancers having their origin in at least the following organs or tissues, regardless of histologic subtype: breast; tissues of the male and female urogenital system (e.g. ureter, bladder, prostate, testis, ovary, cervix, uterus, vagina); lung; tissues of the gastrointestinal system (e.g., stomach, large and small intestine, colon, rectum); exocrine glands such as the pancreas and adrenals; tissues of the mouth and esophagus; brain and spinal cord; kidney (renal); pancreas; hepatobiliary system (e.g., liver, gall bladder); lymphatic system; smooth and striated muscle; bone and bone marrow; skin; and tissues of the eye.

Furthermore, the present compounds are believed effective in treating cancers or tumors in any prognostic stage of development, as measured, for example, by the "Overall Stage Groupings" (also called "Roman Numeral") or the Tumor, Nodes, and Metastases (TNM) staging systems. Appropriate prognostic staging systems and stage descriptions for a given cancer are known in the art, for example as described in http://cancernet.nci.nih.gov/pdq/pdq_treatment.shtml, supra. The compounds do not kill normal cells in concentrations at which tumor cells are killed.

The compounds are also believed useful in the treatment of non-cancer proliferative disorders. Non-cancer proliferative disorders are characterized by the uncontrolled growth of cells with a benign phenotype, meaning that the cells evade only the normal controls on growth, but cannot metastasize. Non-cancer proliferative disorders which may be treated with the present compounds include, but are not limited to, the following: hemangiomatosis in newborn; secondary progressive multiple sclerosis; chronic progressive myelodegenerative disease; neurofibromatosis; ganglioneuromatosis; keloid formation; Paget's Disease of the bone; fibrocystic disease (e.g., of the breast or uterus); sarcoidosis; Peronies and Duputren's fibrosis, cirrhosis, atherosclerosis and vascular restenosis.

Treatment of this broad range of tumor cells with the styryl benzylsulfone compounds of the invention leads to inhibition of cell proliferation and induction of apoptotic cell death.

Tumor cells treated with the compounds of the invention accumulate in the G2/M phase of the cell cycle. As the cells exit the G2/M phase, they appear to undergo apoptosis. Treatment of normal cells with the styryl benzylsulfones does not result in apoptosis.

The (E)-styryl benzylsulfones of the present invention may be prepared by Knoevenagel condensation of aromatic aldehydes with benzylsulfonyl acetic acids. The procedure is described by Reddy et al., *Acta. Chim. Hung.* 115:269–71

(1984); Reddy et al., *Sulfur Letters* 13:83–90 (1991); Reddy et al., *Synthesis* No. 4, 322–323 (1984); and Reddy et al., *Sulfur Letters* 7:43–48 (1987), the entire disclosures of which are incorporated herein by reference.

According to the Scheme 1 below, $R_a$ represents mono- or di-substitution. Similarly, $R_b$ represents mono- or di-substitution. The benzyl thioacetic acid B is formed by the reaction of sodium thioglycollate and a benzyl chloride A. The benzyl thioacetic acid B is then oxidized with 30% hydrogen peroxide to give a corresponding benzylsulfonyl acetic acid C. Condensation of the benzylsulfonyl acetic acid C with an aromatic aldehyde D via a Knoevenagel reaction in the presence of benzylamine and glacial acetic acid yields the desired (E)-styryl benzylsulfone E.

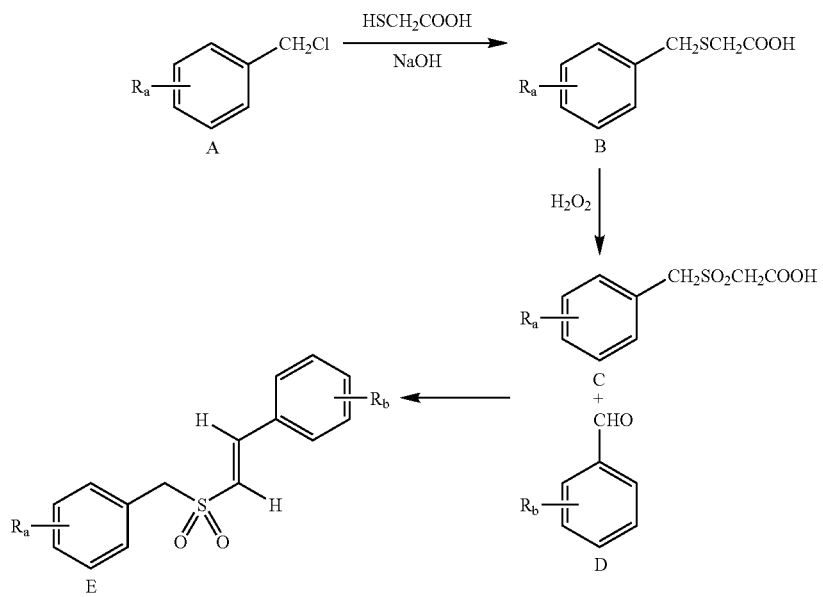

The following is a more detailed two-part synthesis procedure for preparing (E)-styryl benzylsulfones according to the above scheme.

General Procedure 1: Synthesis (E)-Styryl Benzylsulfones

Part A. To a solution of (8 g, 0.2 mol) sodium hydroxide in methanol (200 ml), thioglycollic acid (0.1 mol) is added slowly and the precipitate formed is dissolved by stirring the contents of the flask. Then an appropriately substituted benzyl chloride (0.1 mol) is added stepwise and the reaction mixture is refluxed for 2–3 hours. The cooled contents are poured onto crushed ice and neutralized with dilute hydrochloric acid (200 ml). The resulting corresponding benzylthioacetic acid (0.1 mol) is subjected to oxidation with 30% hydrogen peroxide (0.12 mol) in glacial acetic acid (125 ml) by refluxing for 1 hour. The contents are cooled and poured onto crushed ice. The separated solid is recrystalized from hot water to give the corresponding pure benzylsulfonylacetic acid.

Part B. A mixture of the benzylsulfonyl acetic acid (10 mmol), an appropriately substituted aromatic aldehyde (10 mmol), and benzylamine (200 ml) in glacial acetic acid (12 ml) is refluxed for 2–3 hours. The contents are cooled and treated with cold ether (50 ml). Any product precipitated out is separated by filtration. The filtrate is diluted with more ether and washed successively with a saturated solution of sodium bicarbonate (20 ml), sodium bisulfite (20 ml), dilute hydrochloric acid (20 ml) and finally with water (35 ml). Evaporation of the dried ethereal layer yields styryl benzylsulfones as a solid material.

According to an alternative to Part A, the appropriate benzylsulfonylacetic acids may be generated by substituting a thioglycollate $HSCH_2COOR$ for thioglycollic acid, where R is an alkyl group, typically C1–C6 alkyl. This leads to the formation of the alkylbenzylthioacetate intermediate (F),

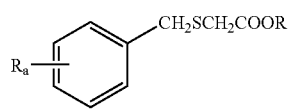

which is then converted to the corresponding benzyl thioacetic acid B by alkaline or acid hydrolysis.

The styryl benzylsulfone compounds of the present invention may be derivatized with a chemical group to permit conjugation to a carrier molecule, for the purpose of raising antibodies to the styryl sulfones. Suitable derivatizing chemistries are well known to those skilled in the art. Preferably, the derivative comprises a carboxylic acid derivative. The carrier may comprise any molecule sufficiently large to be capable of generating an immune response in an appropriate host animal. One such preferred carrier is keyhole limpet haemocyanin (KLH).

The compounds of the present invention may take the form or pharmaceutically acceptable salts. The term "pharmaceutically acceptable salts", embraces salts commonly used to form alkali metal salts and to form addition salts of free acids or free bases. The nature of the salt is not critical, provided that it is pharmaceutically acceptable. Suitable pharmaceutically acceptable acid addition salts may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicyclic, salicyclic, 4-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, stearic, algenic, beta-hydroxybutyric, salicyclic, galactaric and galacturonic acid. Suitable pharmaceutically acceptable base addition salts of compounds of formula I or II include metallic salts made from calcium, lithium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts may be prepared by conventional means from the corresponding compound of formula I or II by reacting, for example, the appropriate acid or base with the compound of formula I or II.

The compounds of the invention may be administered in the form of a pharmaceutical composition, in combination with a pharmaceutically acceptable carrier. The active ingredient in such formulations may comprise from 0.1 to 99.99 weight percent. By "pharmaceutically acceptable carrier" is meant any carrier, diluent or excipient which is compatible with the other ingredients of the formulation and to deleterious to the recipient.

The compounds of the invention may be administered to individuals (mammals, including animals and humans) afflicted with cancer.

The compounds are also useful in the treatment of non-cancer proliferative disorders, that is, proliferative disorders which are characterized by benign indications. Such disorders may also be known as "cytoproliferative" or "hyperproliferative" in that cells are made by the body at an atypically elevated rate, but do not escape normal position controls (i.e., have no metastatic potential). Such disorders include, but are not limited to, the following: hemangiomatosis in newborn; secondary progressive multiple sclerosis; chronic progressive myelodegenerative disease; neurofibromatosis; ganglioneuromatosis; keloid formation; Paget's Disease of the bone; fibrocystic disease (e.g., of the breast or uterus); sarcoidosis; Peronies and Duputren's fibrosis, cirrhosis, atherosclerosis and vascular restenosis.

The compounds may be administered by any route, including oral and parenteral administration. Parenteral administration includes, for example, intravenous, intramuscular, intraarterial, intraperitoneal, intranasal, rectal, intravaginal, intravesical (e.g., to the bladder), intradermal, topical or subcutaneous administration. Also contemplated within the scope of the invention is the instillation of drug in the body of the patient in a controlled formulation, with systemic or local release of the drug to occur at a later time. For example, the drug may localized in a depot for controlled release to the circulation, or for release to a local site of tumor growth.

The active agent is preferably administered with a pharmaceutically acceptable carrier selected on the basis of the selected route of administration and standard pharmaceutical practice. The active agent may be formulated into dosage forms according to standard practices in the field of pharmaceutical preparations. See Alphonso Gennaro, ed., *Remington's Pharmaceutical Sciences,* 18th Ed., (1990) Mack Publishing Co., Easton, Pa. Suitable dosage forms may comprise, for example, tablets, capsules, solutions, parenteral solutions, troches, suppositories, or suspensions.

For parenteral administration, the active agent may be mixed with a suitable carrier or diluent such as water, an oil (particularly a vegetable oil), ethanol, saline solution, aqueous dextrose (glucose) and related sugar solutions, glycerol, or a glycol such as propylene glycol or polyethylene glycol. Solutions for parenteral administration preferably contain a water soluble salt of the active agent. Stabilizing agents, antioxidizing agents and preservatives may also be added. Suitable antioxidizing agents include sulfite, ascorbic acid, citric acid and its salts, and sodium EDTA. Suitable preservatives include benzalkonium chloride, methyl- or propylparaben, and chlorbutanol. The composition for parenteral administration may take the form of an aqueous or nonaqueous solution, dispersion, suspension or emulsion.

For oral administration, the active agent may be combined with one or more solid inactive ingredients for the preparation of tablets, capsules, pills, powders, granules or other suitable oral dosage forms. For example, the active agent may be combined with at least one excipient such as fillers, binders, humectants, disintegrating agents, solution retarders, absorption accelerators, wetting agents absorbents or lubricating agents. According to one tablet embodiment, the active agent may be combined with carboxymethylcellulose calcium, magnesium stearate, mannitol and starch, and then formed into tablets by conventional tableting methods.

The specific dose of compound according to the invention to obtain therapeutic benefit will, of course, be determined by the particular circumstances of the individual patient including, the size, weight, age and sex of the patient, the nature and stage of the disease, the aggressiveness of the disease, and the route of administration. For example, a daily dosage of from about 0.05 to about 50 mg/kg/day may be utilized. Higher or lower doses are also contemplated.

The practice of the invention is illustrated by the following non-limiting examples. In each of the following examples, the substituted benzylsulfonyl acetic acid was made according to Part A of General Procedure 1: Synthesis (E)-Styryl Benzylsulfones, above. The styryl benzylsulfone compounds were recrystalized from 2-propanol and the purity was checked by thin layer chromatography.

EXAMPLE 1

(E)-3-Hydroxy-4-nitrostyryl-4-chlorobenzylsulfone

A solution of 4-chlorobenzylsulfonylacetic acid (10 mmol) and 3-hydroxy-4-nitrobenzaldehyde (10 mmol) was subjected to General Procedure 1, Part B. The title compound, melting point 216–219° C., was obtained in 58% yield.

EXAMPLE 2

(E)-2-Amino-5-chlorostyryl-4-chlorobenzylsulfone

A solution of 4-chlorobenzylsulfonylacetic acid (10 mmol) and 2-amino-5-chlorobenzaldehyde (10 mmol) was subjected to General Procedure 1, Part B. The title compound, melting point 174–176° C., was obtained in 58% yield.

EXAMPLE 3

(E)-3-Methyl-4-fluorostyryl-4-chlorobenzylsulfone

A solution of 4-chlorobenzylsulfonylacetic acid (10 mmol) and 3-methyl-4-fluorobenzaldehyde (10 mmol) was subjected to General Procedure 1, Part B. The title compound, melting point 169–171° C., was obtained in 63% yield.

EXAMPLE 4

(E)-2,6-Dimethoxystyryl-4-chlorobenzylsulfone

A solution of 4-chlorobenzylsulfonylacetic acid (10 mmol) and 2,6-dimethoxybenzaldehyde (10 mmol) was subjected to General Procedure 1, Part B. The title compound, melting point 157–159° C., was obtained in 60% yield.

EXAMPLE 5

(E)-2-Amino-5-chlorostyryl-4-bromobenzylsulfone

A solution of 4-bromobenzylsulfonylacetic acid (10 mmol) and 2-amino-5-chlorobenzaldehyde (10 mmol) was subjected to General Procedure 1, Part B. The title compound, melting point 162–163° C., was obtained in 52% yield.

EXAMPLE 6

(E)-2,6-Dimethoxystyryl-4-bromobenzylsulfone

A solution of 4-bromobenzylsulfonylacetic acid (10 mmol) and 2,6-dimethoxylbenzaldehyde (10 mmol) was subjected to General Procedure 1, Part B. The title compound, melting point 165–168° C., was obtained in 64% yield.

EXAMPLE 7

(E)-3-Hydroxy-4-fluorostyryl-4-bromobenzylsulfone

A solution of 4-bromobenzylsulfonylacetic acid (10 mmol) and 3-hydroxy-4-fluorobenzaldehyde (10 mmol) was subjected to General Procedure 1, Part B. The title compound, melting point 148–150° C., was obtained in 50% yield.

EXAMPLE 8

(E)-3-Methoxy-4-fluorostyryl-4-bromobenzylsulfone

A solution of 4-bromobenzylsulfonylacetic acid (10 mmol) and 3-methoxy-4-fluorobenzaldehyde (10 mmol) was subjected to General Procedure 1, Part B. The title compound, melting point 153–155° C., was obtained in 51% yield.

EXAMPLE 9

(E)-2-Amino-5-chlorostyryl-4-fluorobenzylsulfone

A solution of 4-fluorobenzylsulfonylacetic acid (10 mmol) and 2-amino-5-chlorobenzaldehyde (10 mmol) was subjected to General Procedure 1, Part B. The title compound, melting point 157–158° C., was obtained in 51% yield.

EXAMPLE 10

(E)-2-Hydroxy-3-ethoxystyryl-4-methoxybenzylsulfone

A solution of 4-methoxybenzylsulfonylacetic acid (10 mmol) and 2-hydroxy-3-ethoxybenzaldehyde (10 mmol) was subjected to General Procedure 1, Part B. The title compound, melting point 207–209° C., was obtained in 56% yield.

EXAMPLE 11

(E)-3-Ethoxy-4-hydroxystyryl-4-methoxybenzylsulfone

A solution of 4-methoxybenzylsulfonylacetic acid (10 mmol) and 3-ethoxy-4-hydroxybenzaldehyde (10 mmol) was subjected to General Procedure 1, Part B. The title compound, melting point 160–161° C., was obtained in 54% yield.

EXAMPLE 12

(E)-3-Methoxy-4-ethoxystyryl-4-methoxybenzylsulfone

A solution of 4-methoxybenzylsulfonylacetic acid (10 mmol) and 3-methoxy-4-ethoxybenzaldehyde (10 mmol) was subjected to General Procedure 1, Part B. The title compound, melting point 128–130° C., was obtained in 57% yield.

EXAMPLE 13

(E)-2,6-Dimethoxystyryl-4-methoxybenzylsulfone

A solution of 4-methoxybenzylsulfonylacetic acid (10 mmol) and 2,6-dimethoxybenzaldehyde (10 mmol) was subjected to General Procedure 1, Part B. The title compound, melting point 136–138° C., was obtained in 51% yield.

EXAMPLE 14

(E)-2,4-Dimethoxystyryl-4-methoxybenzylsulfone

A solution of 4-methoxybenzylsulfonylacetic acid (10 mmol) and 2,4-dimethoxybenzaldehyde (10 mmol) was subjected to General Procedure 1, Part B. The title compound, melting point 161–162° C., was obtained in 59% yield.

EXAMPLE 15

(E)-3,5-Dimethoxystyryl-4-methoxybenzylsulfone

A solution of 4-methoxybenzylsulfonylacetic acid (10 mmol) and 3,5-dimethoxybenzaldehyde (10 mmol) was subjected to General Procedure 1, Part B. The title compound, melting point 119–121° C., was obtained in 62% yield.

EXAMPLE 16

(E)-2,5-Dimethoxystyryl-4-methoxybenzylsulfone

A solution of 4-methoxybenzylsulfonylacetic acid (10 mmol) and 2,5-dimethoxybenzaldehyde (10 mmol) was subjected to General Procedure 1, Part B. The title compound, melting point 105–107° C., was obtained in 54% yield.

EXAMPLE 17

(E)-2,3-Dimethoxystyryl-4-methoxybenzylsulfone

A solution of 4-methoxybenzylsulfonylacetic acid (10 mmol) and 2,3-dimethoxybenzaldehyde (10 mmol) was subjected to General Procedure 1, Part B. The title compound, melting point 114–116° C., was obtained in 56% yield.

EXAMPLE 18

(E)-3,4-Dimethoxystyryl-4-methoxybenzylsulfone

A solution of 4-methoxybenzylsulfonylacetic acid (10 mmol) and 3,4-dimethoxybenzaldehyde (10 mmol) was subjected to General Procedure 1, Part B. The title compound, melting point 160–161° C., was obtained in 54% yield.

EXAMPLE 19

(E)-2-Nitro-3-methoxystyryl-4-methoxybenzylsulfone

A solution of 4-methoxybenzylsulfonylacetic acid (10 mmol) and 2-nitro-3-methoxybenzaldehyde (10 mmol) was subjected to General Procedure 1, Part B. The title compound, melting point 145–147° C., was obtained in 52% yield.

EXAMPLE 20

(E)-2,4-Dimethystyryl-4-methoxybenzylsulfone

A solution of 4-methoxybenzylsulfonylacetic acid (10 mmol) and 2,4-dimethybenzaldehyde (10 mmol) was subjected to General Procedure 1, Part B. The title compound, melting point 126–128° C., was obtained in 55% yield.

EXAMPLE 21

(E)-2,6-Dimethystyryl-4-methoxybenzylsulfone

A solution of 4-methoxybenzylsulfonylacetic acid (10 mmol) and 2,6-dimethybenzaldehyde (10 mmol) was subjected to General Procedure 1, Part B. The title compound, melting point 99–101° C., was obtained in 53% yield.

EXAMPLE 22

(E)-2,3-Dimethystyryl-4-methoxybenzylsulfone

A solution of 4-methoxybenzylsulfonylacetic acid (10 mmol) and 2,3-dimethybenzaldehyde (10 mmol) was subjected to General Procedure 1, Part B. The title compound, melting point 105–107° C., was obtained in 57% yield.

EXAMPLE 23

(E)-3,5-Dimethystyryl-4-methoxybenzylsulfone

A solution of 4-methoxybenzylsulfonylacetic acid (10 mmol) and 3,5-dimethybenzaldehyde (10 mmol) was subjected to General Procedure 1, Part B. The title compound, melting point 127–130° C., was obtained in 58% yield.

EXAMPLE 24

(E)-2,4-Diethoxystyryl-4-methoxybenzylsulfone

A solution of 4-methoxybenzylsulfonylacetic acid (10 mmol) and 2,4-diethoxybenzaldehyde (10 mmol) was subjected to General Procedure 1, Part B. The title compound, melting point 89–93° C., was obtained in 56% yield.

EXAMPLE 25

(E)-2,5-Diethoxystyryl-4-methoxybenzylsulfone

A solution of 4-methoxybenzylsulfonylacetic acid (10 mmol) and 2,5-diethoxybenzaldehyde (10 mmol) was subjected to General Procedure 1, Part B. The title compound, melting point 89–92° C., was obtained in 53% yield.

EXAMPLE 26

(E)-3-Methoxy-4-fluorostyryl-4-methoxybenzylsulfone

A solution of 4-methoxybenzylsulfonylacetic acid (10 mmol) and 3-methoxy-4-fluorobenzaldehyde (10 mmol) was subjected to General Procedure 1, Part B. The title compound, melting point 105–107° C., was obtained in 55% yield.

EXAMPLE 27

(E)-2-Amino-5-chlorostyryl-4-methoxybenzylsulfone

A solution of 4-methoxybenzylsulfonylacetic acid (10 mmol) and 2-amino-5-chlorobenzaldehyde (10 mmol) was subjected to General Procedure 1, Part B. The title compound, melting point 162–165° C. was obtained in 52% yield.

EXAMPLE 28

(E)-2-Amino-5-chlorostyryl-4-nitrobenzylsulfone

A solution of 4-nitrobenzylsulfonylacetic acid (10 mmol) and 2-amino-5-chlorobenzaldehyde (10 mmol) was subjected to General Procedure 1, Part B. The title compound, melting point 191–193° C., was obtained in 52% yield.

EXAMPLE 29

(E)-2,6-Dimethoxystyryl-4-nitrobenzylsulfone

A solution of 4-nitrobenzylsulfonylacetic acid (10 mmol) and 2,6-dimethoxybenzaldehyde (10 mmol) was subjected to General Procedure 1, Part B. The title compound, melting point 164–167° C., was obtained in 68% yield.

EXAMPLE 30

(E)-4-Iodostyryl-2-methoxy-5-nitrobenzylsulfone

A solution of 2-methoxy-5-nitrobenzylsulfonylacetic acid (10 mmol) and 4-iodobenzaldehyde (10 mmol) was subjected to General Procedure 1, Part B. The title compound, melting point 218–221° C., was obtained in 61% yield.

EXAMPLE 31

(E)-4-Bromostyryl-2-methoxy-5-nitrobenzylsulfone

A solution of 2-methoxy-5-nitrobenzylsulfonylacetic acid (10 mmol) and 4-bromobenzaldehyde (10 mmol) was subjected to General Procedure 1, Part B. The title compound, melting point 166–168° C., was obtained in 57% yield.

EXAMPLE 32

(E)$_4$–Chlorostyryl-2-methoxy-5-nitrobenzylsulfone

A solution of 2-methoxy-5-nitrobenzylsulfonylacetic acid (10 mmol) and 4-chlorobenzaldehyde (10 mmol) was subjected to General Procedure 1, Part B. The title compound, melting point 157–159° C., was obtained in 59% yield.

EXAMPLE 33

(E)-4-Fluorostyryl-2-methoxy-5-nitrobenzylsulfone

A solution of 2-methoxy-5-nitrobenzylsulfonylacetic acid (10 mmol) and 4-fluorobenzaldehyde (10 mmol) was subjected to General Procedure 1, Part B. The title compound, melting point 187–189° C., was obtained in 53% yield.

EXAMPLE 34

(E)-4-Nitrostyryl-2-methoxy-5-nitrobenzylsulfone

A solution of 2-methoxy-5-nitrobenzylsulfonylacetic acid (10 mmol) and 4-nitrobenzaldehyde (10 mmol) was subjected to General Procedure 1, Part B. The title compound, melting point 196–198° C., was obtained in 53% yield.

EXAMPLE 35

(E)-2-Methoxystyryl-2,6-dimethoxybenzylsulfone

A solution of 2,6-dimethoxybenzylsulfonylacetic acid (10 mmol) and 2-methoxybenzaldehyde (10 mmol) is subjected to General Procedure 1, Part B. The title compound is obtained.

EXAMPLE 36

(E)-4-Fluorostyryl-2,6-dimethoxybenzylsulfone

A solution of 2,6-dimethoxybenzylsulfonylacetic acid (10 mmol) and 4-fluorobenzaldehyde (10 mmol) is subjected to General Procedure 1, Part B. The title compound is obtained.

EXAMPLE 37

(E)-2-Nitrostyryl-2,4-dichlorobenzylsulfone

A solution of 2,4-dichlorobenzylsulfonylacetic acid (10 mmol) and 2-nitrobenzaldehyde (10 mmol) was subjected to the General Procedure 1, Part B. The title compound, melting point 153–155° C., was obtained in 58% yield.

EXAMPLE 38

(E)-3-Nitrostyryl-2,4-dichlorobenzylsulfone

A solution of 2,4-dichlorobenzylsulfonylacetic acid (10 mmol) and 3-nitrobenzaldehyde (10 mmol) was subjected to the General Procedure 1, Part B. The title compound, melting point 161–163° C., was obtained in 54% yield.

EXAMPLE 39

(E)-2,6-Dimethoxystyryl-2-methoxybenzylsulfone

A solution of 2-methoxybenzylsulfonylacetic acid (10 mmol) and 2,6-dimethoxybenzaldehyde (10 mmol) was subjected to the General Procedure 1, Part B. The title compound, melting point 163–165° C., was obtained in 52% yield.

EXAMPLE 40

Effect of (E)-2,6-Dimethoxystyryl-4-methoxybenzylsulfone on Tumor Cell Lines

A. Cells.

The effect of the Example 13 compound on the growth of normal fibroblasts and on tumor cells of prostate, colon, lung, brain, pancreas and breast origin was examined utilizing the following cell lines: prostate carcinoma cell line DU-145; colorectal carcinoma cell line DLD-1; non-small cell lung carcinoma cell line H157; pancreatic carcinoma cell line MIA-Pa-Ca-2; glioblastoma cell line U87; and breast adenocarcinoma cell line BT-20. BT-20 is an estrogen-unresponsive cell line. NIH/3T3 and HFL are normal murine and human fibroblasts, respectively. BT-20, DLD-1 and H157 were grown in Dulbecco's modified Eagle's medium (DMEM) containing 10% fetal bovine serum supplemented with penicillin and streptomycin. DU145 was cultured in RPMI with 10% fetal bovine serum containing penicillin and streptomycin. NIH3T3 and HFL cells were grown in DMEM containing 10% calf serum supplemented with penicillin and streptomycin. Cells were plated at density levels of $1.0 \times 10^5$ cells per well in six-well plates. Cell cultures were maintained at 37° C. in a humidified atmosphere of 5% $CO_2$.

B. Treatment with Styryl Benzylsulfone and Viability Assay

Cells were treated with the Example 13 compound at concentrations of 100, 250, 500 and 1000 nM. Cell viability was determined after 96 hours by the Trypan blue exclusion method. Values were plotted as the percent of drug-treated cells remaining viable compared to DMSO-treated cells The results are set forth in FIG. 1. The drug G150 (the concentration resulting in 50% growth inhibition) was calculated as 200 nM for the MIA-Pa-Ca-2 cell line.

Normal cells HFL and NIH 3T3 treated with the same compound displayed 5% growth inhibition but no appreciable cell death.

EXAMPLE 41

Effect of (E)-2-Nitrostyryl-2,4-dichlorobenzylsulfone on Tumor Cell Lines

Figure 2:
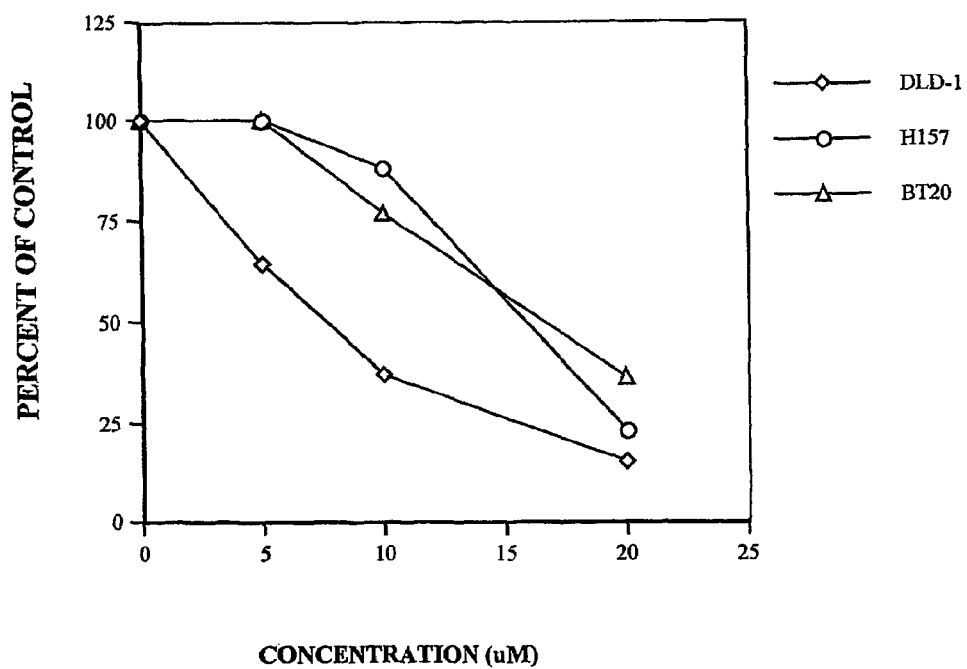
FIG. 2 shows the effect of (E)-2-nitrostyryl-2,4-dichlorobenzylsulfone on the growth of cells of the indicated tumor cell lines. Values are plotted as the percent of drug-treated cells remaining viable compared to DMSO-treated cells of the same type.

The procedure of Example 40 was followed for the compound of Example 37, on cell lines DLD-1, H157 and BT20, at 5, 10 and 20 μM concentrations. The results are shown in FIG. 2. The drug G150 was calculated for each cell line as follows: DLD, 8 μM; H157, 15 μM; and BT20, 15 μM.

All references cited herein are incorporated by reference. The present invention may be embodied in other specific forms without departing from the spirit or essential attributes thereof and, accordingly, reference should be made to the appended claims, rather than to the foregoing specification, as indication the scope of the invention.

The invention claimed is:

1. A compound of the formula:

[Structure I]

wherein:
   $R_1$ is selected from the group consisting of phosphonato, amino, sulfamyl, carboxy, acetoxy, and dimethylamino (C2–C6 alkoxy); and
   $R_2$ and $R_3$ are independently selected from the group consisting of halogen, C1–C6 alkoxy, C1–C6 alkyl, nitro, cyano, hydroxy, phosphonato, amino, sulfamyl, carboxy, acetoxy, and dimethylamino(C2–C6 alkoxy);
   provided:
      $R_2$ may not be 2-halogen when $R_3$ is 4-halogen;
   or a pharmaceutically acceptable salt thereof.

2. A compound according to claim 1 wherein $R_1$ is selected from the group consisting of phosphonato, amino, sulfamyl, acetoxy, and dimethylamino(C2–C6 alkoxy); and $R_2$ and $R_3$ are independently selected from the group consisting of halogen, C1–C6 alkoxy, C1–C6 alkyl, nitro, cyano, hydroxy, phosphonato, amino, sulfamyl, acetoxy, and dimethylamino(C2–C6 alkoxy).

3. A compound of the formula:

[Structure I]

wherein:
   $R_1$ is halogen; and
   $R_2$ and $R_3$ are independently selected from the group consisting of halogen, nitro, cyano, hydroxy, phosphonato, amino, sulfamyl, carboxy, acetoxy, and dimethylamino(C2–C6 alkoxy);
   provided:
      $R_1$ may not be halogen when $R_2$ and $R_3$ are both halogen;
      $R_2$ may not be 2-halogen when $R_3$ is 4-halogen;
   or a pharmaceutically acceptable salt thereof.

4. A compound of the formula:

[Structure I]

wherein:
   $R_1$ is halogen; and
   $R_2$ and $R_3$ are independently selected from the group consisting of C1–C6 alkoxy and C1–C6 alkyl; or a pharmaceutically acceptable salt thereof.

5. A compound according to claim 4, wherein $R_2$ and $R_3$ are C1–C6 alkoxy; or a pharmaceutically acceptable salt thereof.

6. The compound according to claim 3 which is (E)-3-hydroxy-4-nitrostyryl-4-chlorobenzylsulfone, or a pharmaceutically acceptable salt thereof.

7. A pharmaceutical composition comprising a pharmaceutically acceptable carrier and a compound according to claim 1, 3 or 4 or a pharmaceutically acceptable salt of such a compound.

8. A method of treating an individual for a proliferative disorder comprising administering to said individual an effective amount of a compound according to claim 1, 3 or 4 or a pharmaceutically acceptable salt of such a compound.

9. A method according to claim 8 wherein the proliferative disorder is selected from the group consisting of hemangiomatosis in newborn, secondary progressive multiple sclerosis, chronic progressive myelodegenerative disease, neurofibromatosis, ganglioneuromatosis, keloid formation, Paget's Disease of the bone, fibrocystic disease, sarcoidosis, Peronies and Duputren's fibrosis, cirrhosis, atherosclerosis and vascular restenosis.

10. A method according to claim 8 wherein the proliferative disorder is cancer.

11. A method according to claim 10 wherein the cancer is selected from the group of cancers of the ovaries, testis, cervix, uterus, vagina, breast, prostate, lung, kidney, rectum, colon, stomachs adrenal gland, mouth, esophagus, brain, liver, gall bladder, skin, bone, lymphatic system and eye, or the cancer is a hematological neoplasia.

12. A method of inducing apoptosis of tumor cells in an individual afflicted with cancer comprising administering to said individual an effective amount of a compound according to claim 1, 3 or 4 or a pharmaceutically acceptable salt of such a compound.

13. A method according to claim 12 wherein the tumor cells are selected from the group of tumors consisting of tumors of the ovaries, testis, cervix, uterus, vagina, breast, prostate, lung, kidney, rectum, colon, stomach, adrenal gland, mouth, esophagus, brain, liver, gall bladder, skin, bone, lymphatic system and eye.

14. A compound selected from the group consisting of (E)-2-nitrostyryl-2,4-dichlorobenzylsulfone, (E)-3-nitrostyryl-2,4-dichlorobenzylsulfone, (E)-2,6-dimethoxystyryl-2-methoxybenzyl-sulfone, (E)-2,6-dimethoxystyryl-4-methoxy-benzylsulfone, (E)-3-methoxy-4-ethoxystyryl-4-methoxybenzylsulfone 4-nitrostyryl-2-methoxy-5-nitrobenzylsulfone and pharmaceutically acceptable salts thereof.

15. A pharmaceutical composition comprising a pharmaceutically acceptable carrier and a compound according to claim 14, or a pharmaceutically acceptable salt of such a compound.

16. A method of treating an individual for a proliferative disorder comprising administering to said individual an effective amount of a compound according to claim 14, or a pharmaceutically acceptable salt of such a compound.

17. A method according to claim 16 wherein the proliferative disorder is cancer.

18. A method of inducing apoptosis of tumor cells in an individual afflicted with cancer comprising administering to said individual an effective amount of a compound according to claim 14, or a pharmaceutically acceptable salt of such a compound.

* * * * *